United States Patent
Naka

[11] Patent Number: 6,126,636
[45] Date of Patent: Oct. 3, 2000

[54] PROBE POSITIONING METHOD AND DEVICE THEREFOR

[75] Inventor: Michio Naka, Kyoto, Japan

[73] Assignees: Kurashiki Boseki Kabushiki Kaisha, Okayama; Kyoto Daiichi Kagaku Co., Ltd., Kyoto, both of Japan

[21] Appl. No.: 09/145,336

[22] Filed: Sep. 1, 1998

[30] Foreign Application Priority Data

Sep. 1, 1997 [JP] Japan .................................. 9-235985

[51] Int. Cl.⁷ ...................................................... A61M 5/00
[52] U.S. Cl. ............................................................ 604/116
[58] Field of Search .................................... 600/310, 316, 600/365, 407, 417; 128/897; 604/116; 606/130

[56] References Cited

U.S. PATENT DOCUMENTS

| | | | |
|---|---|---|---|
| 4,362,157 | 12/1982 | Keeth ...................................... | 604/116 |
| 5,306,271 | 4/1994 | Zinreich et al. ......................... | 604/116 |
| 5,364,361 | 11/1994 | Battenfield .............................. | 604/116 |
| 5,569,237 | 10/1996 | Beckenstein ............................ | 604/116 |

FOREIGN PATENT DOCUMENTS 8-332181  12/1996  Japan .
9-49794   2/1997   Japan .

Primary Examiner—Max Hindenburg

[57] ABSTRACT

A method of and a device for accurately positioning a measuring means such as a measurement probe relative to that target area of a living body which has a unique marking peculiar to the living body. A transparent sheet member is first applied to the target part, and an image of the unique marking is then transferred onto the transparent sheet member. The transparent sheet member bearing the image of the unique marking is associated with the measuring device so that a subsequent measurement can be performed by the measuring device after the image transferred onto the transparent sheet member has been aligned with the unique marking in the target area.

16 Claims, 9 Drawing Sheets

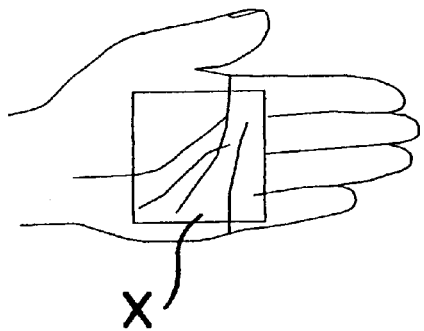
Fig. 1A
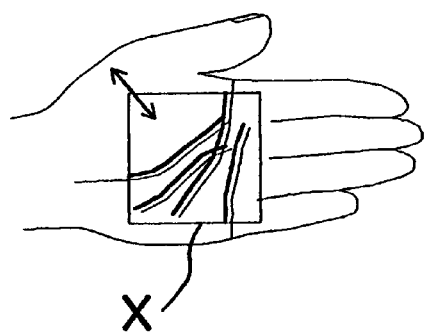
Fig. 1D
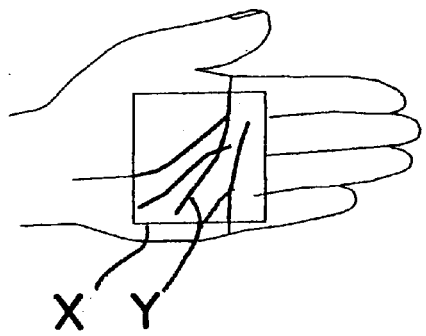
Fig. 1B
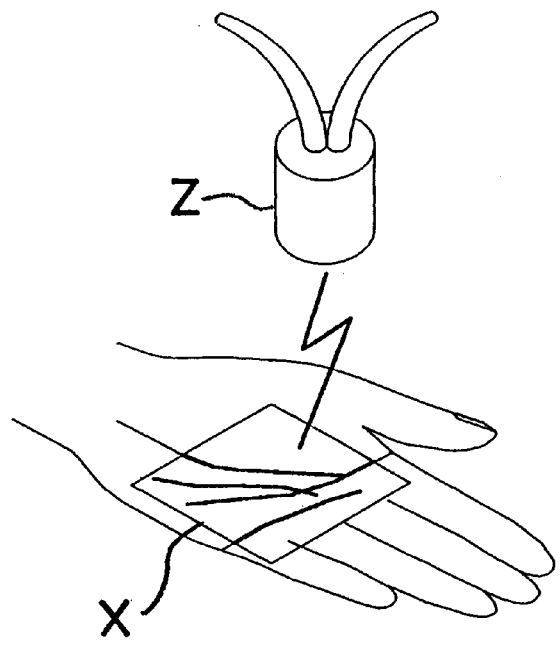
Fig. 1E
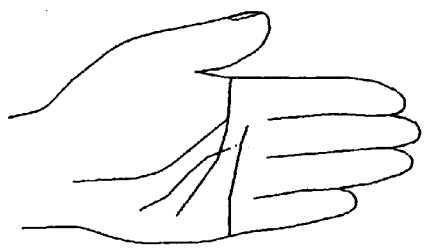
Fig. 1C
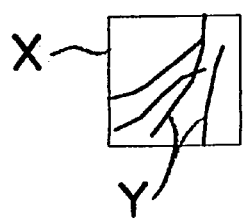

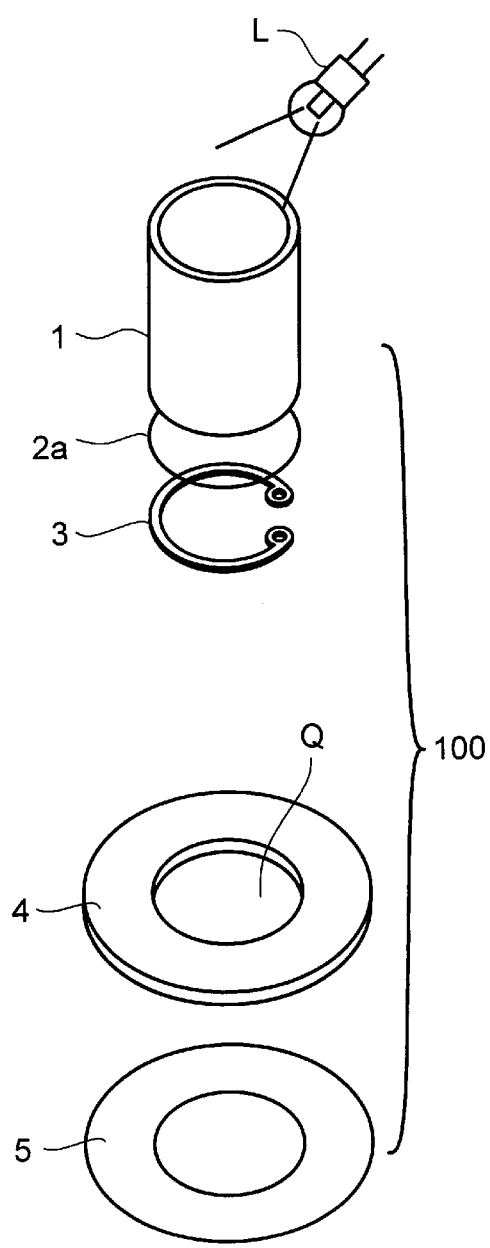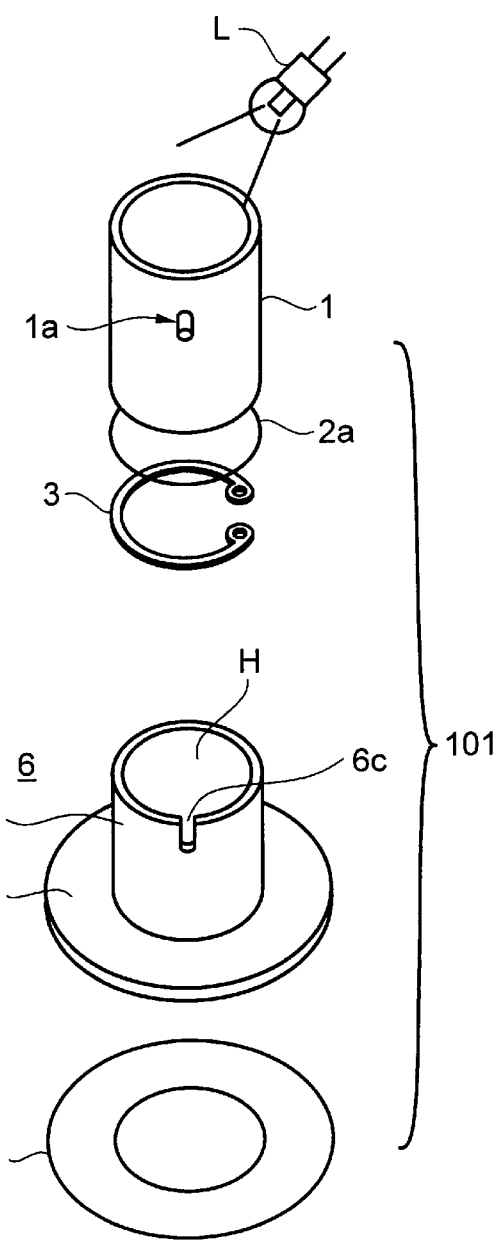

PROBE POSITIONING METHOD AND DEVICE THEREFOR

BACKGROUND OF THE INVENTION

1. Field of the Invention

The present invention generally relates to a method of and a device for positioning a biological measurement probe reproducibly relative to a target part of a living body during noninvasive measurement of a biological data such as, for example, the concentration of a particular component in the living body from such target part. More particularly, the present invention relates to the positioning method and the positioning device by which the biological measurement probe can be positioned reproducibly at the target part of the living body to achieve reproducible placement of the biological measuring probe at substantially the same target part throughout a plurality of cycles of biological data measurement to thereby reduce the chances of measurement error.

2. Description of the Prior Art

The noninvasive measurement of biological data (hereinafter referred to as "biodata") on a particular component in the living body has been studied. For example, the noninvasive measurement of the concentration of, for example, glucose in the living body is generally carried out by illuminating a target part of the living body through a measurement probe, detecting transmitted and/or reflected light from the target part and analyzing a spectrum of the transmitted and/or reflected light so detected. As is well known to those skilled in the art, measurement of the glucose concentration in a diabetic patient is generally performed repeatedly on a regular basis. If the position and/or the angle of the measurement probe relative to the target part of the patient change occasionally each time the biodata measurement is carried out, resulting in change of measurement condition, measurement results will no longer be reliable and be irreproducible. Therefore, the measurement results obtained at a certain time of measurement cannot be utilized for significant comparison with the measurement results obtained previously to determine an exact biological condition of the patient that varies from time to time.

The details of how the results of measurement of the glucose concentration become irreproducible as a result of change in position and/or angle of the measurement probe relative to the target part of the patient are discussed in the Japanese Laid-open Patent Publication No. 8-332181 (corresponding to the published International Application No. WO96/41568 published Dec. 27, 1996, or U.S. patent application Ser. No. 08/776,775 assigned to the same assignees of the present invention) and the Japanese Laid-open Patent publication No. 9-49794 (corresponding to the published International Application No. WO97/06423 published Feb. 20, 1997, or U.S. patent application Ser. No. 08/817,085 assigned to the same assignees of the present invention) with the aid of the experimentally obtained biodata.

Accordingly, this type of biodata measurement requires the measurement probe to be firmly positioned in an exact location each time the measurement is carried out. For this purpose, the Japanese Laid-open Patent Publication No. 9-49794 discloses an intelligent measurement system in which the measurement probe is positioned by the use of an image recognition system whereas the Japanese Laid-open Patent Publication No. 8-332181 discloses preparation of a template having an impression complemental in shape to the shape of the target part of the living body by the use of a plasticizeable material so that during the biodata measurement the target part can be snugly received in the impression in the template to position the target part at an exact location, thereby enabling substantially the same target part of the living body to be remeasured.

It has been found that the intelligent measurement system discussed above requires the use of a CCD camera, an image recognition device and an XYZ drive mechanism, making the system as a whole bulky and expensive. On the other hand, although the positioning by the use of the template as discussed above requires a handy device, preparation of the template often encounters difficulty since the target part is apt to deform if it is that of a living body, and therefore, the use of the template would little result in a satisfactory positioning reproducibility.

SUMMARY OF THE INVENTION

Accordingly, the present invention has been developed to substantially eliminate the above described problems and is intended to provide an improved method of reproducibly positioning a measurement probe at an exact position relative to the target part of the living body each time the biodata measurement is performed with the use of a handy device.

The present invention has an additional object to provide an improved positioning jig for reproducibly positioning a measurement probe at an exact position relative to the target part of the living body each time the biodata measurement is performed.

To accomplish these objects, the present invention according to a broad aspect thereof provides a method of and a device for accurately positioning a measuring means such as a measurement probe relative to that target area of a living body which has a unique marking peculiar to the living body. A transparent sheet member is first applied to the target part, and an image of the unique marking is then transferred onto the transparent sheet member. The transparent sheet member, bearing the image of the unique marking, is associated with the measuring device so that a subsequent measurement can be performed by the measuring device after the image transferred onto the transparent sheet member has been aligned with the unique marking in the target area.

In one preferred embodiment, the device comprises a positioning member having a hole defined therein for accommodating the measuring means, a substantially cylindrical scope having distal and proximal ends opposite to each other and capable of being received in the hole in the positioning member; and a pattern-bearing member bearing an image of the unique marking in the target area of the living body. The pattern-bearing member is adapted to be fitted to the proximal end of the cylindrical scope.

With this device, during a measurement the image on the pattern-bearing member is aligned with the unique marking to enable the same target area to be remeasured each time measurement is performed by the measuring means.

Preferably, the positioning member is a transparent sheet ring or may comprise a tubular member for receiving the measuring means when the latter is inserted in the tubular member. In the latter case, the tubular member having distal and proximal ends opposite to each other is used in combination with either a flat ring member provided at the proximal end of the tubular member, or an annular suction base provided at the proximal end of the tubular member.

According to another aspect of the present invention, the positioning device may comprise a positioning member in the form of an annular transparent sheet having a hole defined therein for accommodating the measuring means and also having an image of the unique marking transferred thereto, such that during a measurement the image on the positioning member is aligned with the unique marking to enable the same target area to be remeasured each time measurement is performed by the measuring means.

In the practice of the method or the device of the present invention, an auxiliary fixing unit may be used which comprises first and second molds adapted to be mated together with the target area sandwiched therebetween to make the target area immovable. The first and second molds have respective recesses defined therein which, when the first and second molds are mated together, define a mold cavity similar to the target area. One of the first and second molds having a through-hole defined therein so as to extend across a wall of such one of the molds for receiving therein the positioning member.

BRIEF DESCRIPTION OF THE DRAWINGS

The present invention will become readily understood from the following description of preferred embodiments thereof made with reference to the accompanying drawings, in which like parts are designated by like reference numeral and in which:

FIGS. 1A to 1E are illustrations showing the principle of positioning a measurement probe relative to a target part, for example, a hand of a living body according to the present invention;

FIG. 2 is an exploded view of a positioning jig according to a first embodiment of the present invention;

FIG. 5 is an exploded view of the positioning jig according to a second embodiment of the present invention;

DETAILED DESCRIPTION OF THE EMBODIMENTS

Figure 3A:
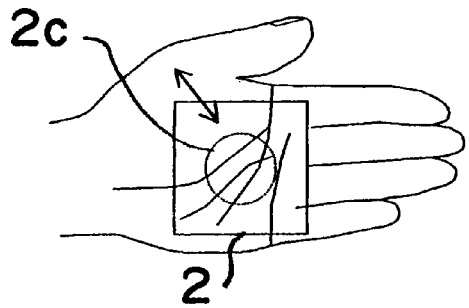
FIGS. 3A to 3G are illustrations showing the sequence of how substantially the same target part of the living body can be aligned with the measurement probe with the use of the positioning jig shown in FIG. 2.

The principle of the present invention will first be described with particular reference to FIGS. 1A to 1E. The present invention in a broad aspect thereof makes use of a transparent pattern-bearing template X which is in the form of a generally rectangular transparent sheet that is immovably applied to a target area of the palm of a hand of a living body, which area is to be examined, as shown in FIG. 1A. After the rectangular transparent sheet has been applied to the hand palm, some of palm lines at the target area to be examined are copied onto the transparent sheet by delineating ink-marked lines following those original palm lines to thereby provide the template X having the palm pattern Y made up of those ink-marked lines as shown in FIG. 1B. FIG. 1C illustrates a condition in which the transparent template X bearing the palm pattern Y is removed from the hand palm, and it will readily be understood that this removed template X can be placed on the hand palm at the same location as it has previously been applied, if the pattern-bearing template X is, after having been reapplied to the hand palm, adjusted in position relative to the hand, as shown in FIG. 1D until the ink-marked lines forming the palm pattern on the transparent template X are aligned with the original lines of the hand palm substantially as shown in FIG. 1B.

Accordingly, by utilizing the pattern-bearing template in association with a measuring means Z as shown in FIG. 1E, and if the pattern-bearing template X is placed on the hand palm with the ink-marked palm lines exactly aligned with the original palm lines in the hand at the time a subsequent cycle of measurement is to be performed, the measuring means Z can be positioned at substantially the same site on the hand palm as that at which the measuring means Z has been placed during the previous cycle of measurement.

To associate the pattern-bearing template with the measuring means Z, the use is preferably made of a generally tubular or bobbin-like scope that can be mounted in a positioning member for holding the measuring means Z. This tubular scope has a lower end to which a cut piece of the pattern-bearing template X is affixed. Alternatively, the positioning member may be the pattern-bearing transparent template having a center region perforated to accommodate therein a measuring probe.

Specific embodiments of the present invention based on the foregoing principle will now be described. Referring to FIG. 2, a positioning jig according to a first embodiment of the present invention is generally identified by 100 and comprises a generally bobbin-like scope 1 having upper and lower open ends opposite to each other. A pattern-bearing disc 2a (See FIG. 3C) cut from a generally rectangular transparent sheet 2 (See FIG. 3A) as will be described later is fitted to the lower open end of the scope 1 by means of a C-clip ring 3. Reference numeral 4 represents a sheet ring formed from a transparent sheet. This sheet ring 4 has a center hole Q defined therein, which hole Q has a diameter substantially equal to the outer diameter of the scope 1 and also to the outer diameter of a measurement probe 11 (See FIG. 3G) as will be described later. This sheet ring 4 is adapted to be bonded to the target area by means of a ring-shaped double-sided adhesive sheet 5, similar in shape to the sheet ring 4, to the target area to be examined.

The manner by which the measurement probe 11 is positioned relative to the target area, for example, a portion of the palm of a patient's hand with the use of the positioning jig 100 shown in FIG. 2 will now be described with particular reference to FIGS. 3A to 3G. In the first place, the rectangular transparent sheet 2 having a circle 2c depicted or otherwise printed thereon is placed on the palm of the hand as shown in FIG. 3A. During the placement of the transparent sheet 2 on the palm, the transparent sheet 2 has to be adjusted in position so that the circle 2c on the transparent sheet 2 may encompass some of the live palm lines which are distinctive and, at the same time, characteristic of the particular patient and which may be a portion of what is termed a palm print.

Figure 3B:
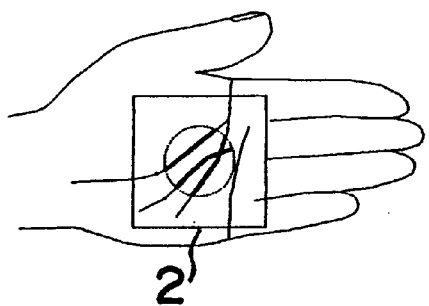
Figure 3C:
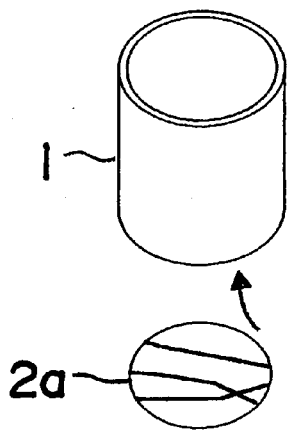

After the placement, at least the distinctive and characteristic palm lines encompassed within the circle 2c are reproduced onto the transparent sheet 2 as shown in FIG. 3B. This reproduction may be accomplished by delineating line images along the live palm lines by the use of an writing instruments, copying or photographing or any other method effective to allow the palm print to be transferred onto the transparent sheet 2. Thus, it will readily be seen that a portion of the transparent sheet 2 encompassed within the circle 2c bears the line images complemental to the live palm lines in the patient's hand. Substantially as shown in FIG. 3C, the transparent sheet 2 is subsequently cut along the circle 2c to provide the pattern-bearing disc 2a which is in turn fitted to a lower end of the scope 1 as shown in FIG. 3C.

Figure 3D:
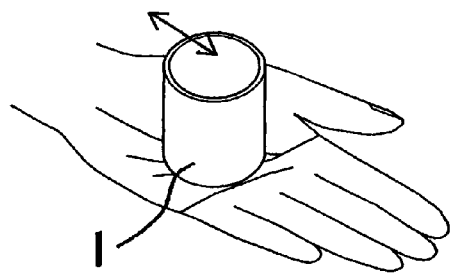

Then, as shown in FIG. 3D, the scope having the pattern-bearing disc 2a fitted to the lower end thereof is mounted on the palm of the patient's hand with the pattern-bearing disc 2a held in contact therewith. At this time, the scope 1 has to be adjusted in position so that the palm line images on the pattern-bearing disc 2a can exactly align with the respective live palm lines which have been utilized to depict the palm line images on the transparent sheet 2. This can be readily accomplished by looking at the pattern-bearing disc 2a with naked eyes through the hollow of the scope 1. Considering that the hollow within the scope 1 may be dark as is true of the scope having a substantial length, alignment of the line images on the pattern-bearing disc 2a with the live palm lines can readily be facilitated if an electric midget lamp is installed inside the scope 1 to illuminate the pattern-bearing disc 2a.

Figure 3E:
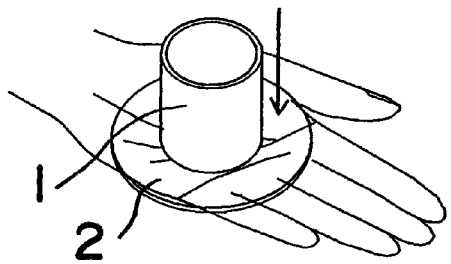

After the positioning of the scope 1 relative to the hand palm, the sheet ring 4 having the center hole Q of a diameter substantially equal to the outer diameter of the scope 1 is placed on the hand palm by passing the scope 1 through the center hole Q as shown in FIG. 3E. It is, however, to be noted that prior to the placement of the sheet ring 4 on the hand palm, the ring-shaped double-adhesive sheet 5 (FIG. 1) similar in shape to the sheet ring 4 is bonded to one of opposite annular surfaces of the sheet ring 4 which may be held in contact with the hand palm. Accordingly, upon placement of the sheet ring 4 on the hand palm with the scope 1 extending through the center hole Q, the sheet ring 4 is bonded to the hand palm. As an alternative to the use of the double-sided adhesive sheet 5, the sheet ring 4 once placed on the hand palm in the manner described above may be fixed in position on the hand palm by means of one or two lengths of a single-sided adhesive tape.

Figure 3F:
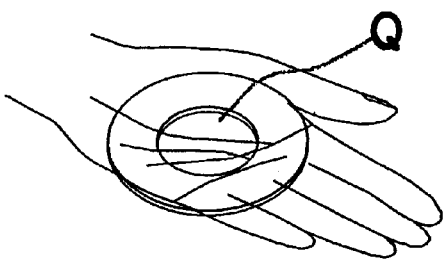
Figure 3G:
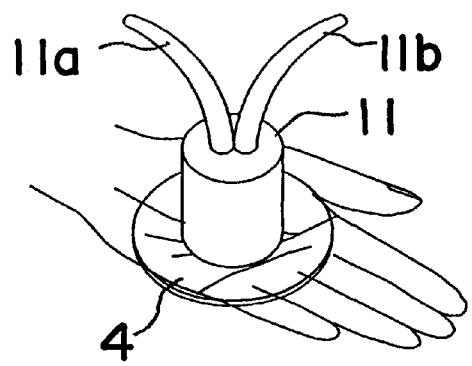

The scope 1 is subsequently removed from the hand, leaving the sheet ring 4 sticking to the hand palm as shown in FIG. 3F, and thereafter the measurement probe 11 having distal and proximal ends opposite to each other and also having light emitting and receiving windows at the proximal end is placed on the hand palm with the proximal end thereof positioned radially immovably inside the center hole Q of the sheet ring 4 as shown in FIG. 3G. Reference numerals 11a and 11b represent respective optical fiber extending outwardly from the distal end of the measurement probe 11 and optically coupled with light emitting and receiving elements (not shown).

A first cycle of biodata measurement is then carried out with the measurement probe 11 positioned on the hand palm in the manner described above and shown in FIG. 3G. After this first cycle of measurement, the scope 1 used is stored for the time to come to perform a subsequent cycle of biodata measurement. However, the scope 1 having the pattern-bearing disc 2a peculiar to the particular patient must be labeled in any suitable manner to avoid the possibility of the scope 1 being used in association with a different patient. The sheet ring 4 being inexpensive may be disposed of.

When time comes to perform the subsequent cycle of biodata measurement, the scope 1 once stored should be re-used and the sequence from the step shown in FIG. 3D to the step shown in FIG. 3G is repeated. This is true even when further cycles of biodata measurement are to be individually performed on a chronological basis. Thus, it will readily be seen that each time the target area of the living body is measured, the measurement probe 11 can be positioned reproducibly in an exact location, thereby enabling substantially the same target area to be reexamined.

Figure 4:
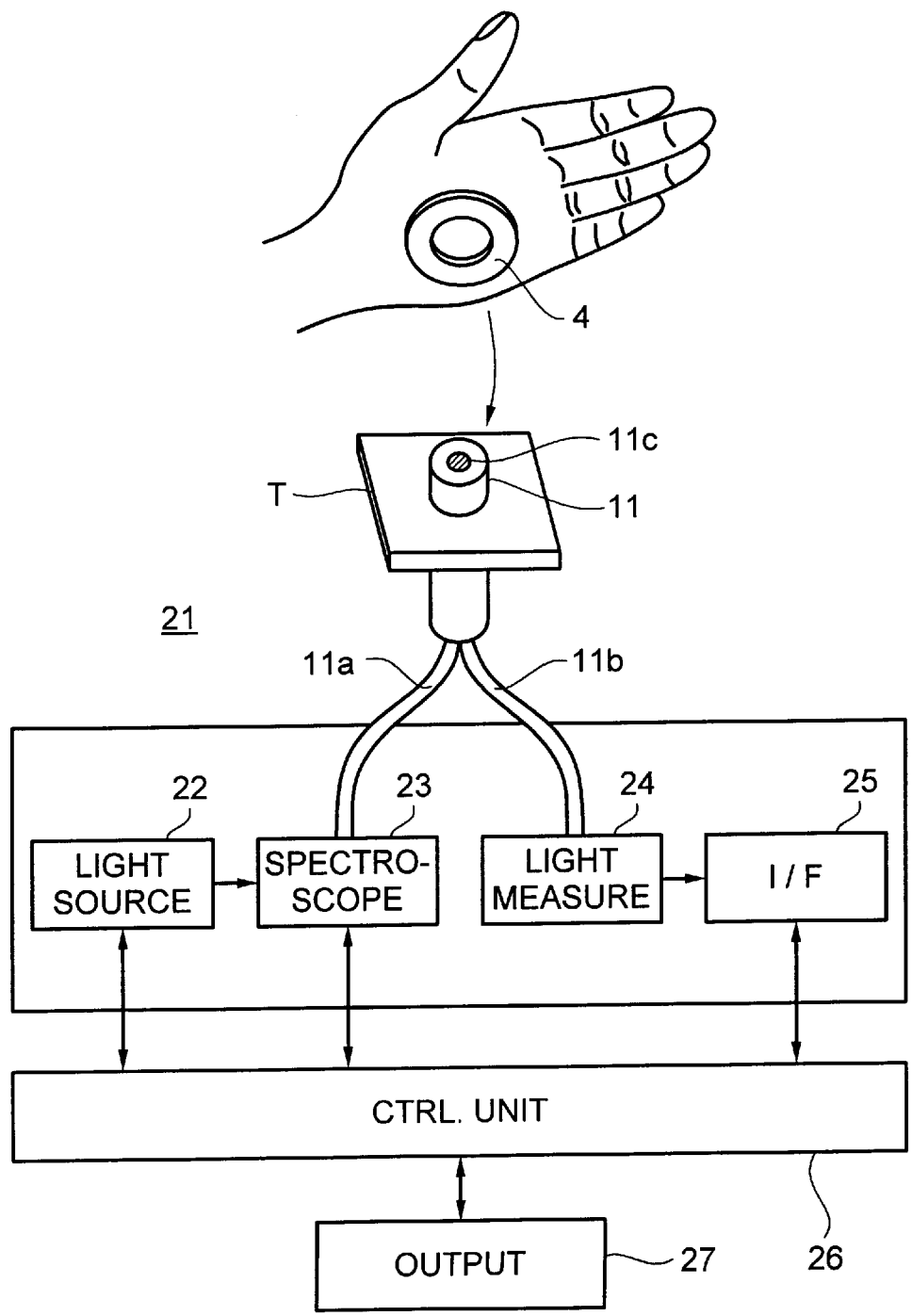
FIG. 4 is a block diagram showing an optical biodata measuring apparatus in which the positioning jig of FIG. 2 is employed.

In the foregoing embodiment of the present invention, the scope 1 having the pattern-bearing disc 2a has been described and shown as placed on the hand palm. In place of the scope 1 being placed on the hand palm, the hand may be placed on a support plate T as shown in FIG. 4. In the example shown in FIG. 4, the measurement probe 11 has a light emitting and receiving window 11c defined at the proximal end face for passage of light outwardly and inwardly therethrough. This measuring probe 11 is fixedly secured to the support plate T with the proximal end thereof protruding a distance upwardly from the support plate T so that when the hand is placed on the support plate T, the center hole Q in the sheet ring 4 sticking to the hand palm can receive the proximal end of the probe 11 to thereby immovably position the measurement probe 11 relative to the hand.

FIG. 4 also illustrates an electro-optical biodata measuring device 21 which comprises a light source 22 for providing a light output for measurement use, a spectroscope 23 for extracting a light component of a desired wavelength and a desired intensity from the light output emitted by the light source 22 and for projecting the light component onto the target area through the measurement probe 11 by way of the optical fiber 11a, a light measuring unit 24, an interface 25 and an arithmetic control unit 26.

The light component emerging outwardly from the light emitting window of the measurement probe 11 illuminates the target area and is then reflected therefrom or transmitted therethrough, the reflected or transmitted light being subsequently received by the light measuring unit 24 through the light receiving window of the measurement probe 11 by way of the optical fiber 11b. Upon receipt of the reflected or transmitted light, the light measuring unit 24 measures the intensity of the reflected or transmitted light. The measured intensity is subsequently supplied through the interface 25 to the arithmetic control unit 26 which provides a measured biodata. The measured biodata may be obtained from an output unit 27 which may comprise one or a combination of a printer, a recorder and a display device.

The positioning jig, now identified by 101, according to a second embodiment of the present invention is shown in FIG. 5. The scope 1 shown therein has a positioning pin 1a secured thereto so as to protrude radially outwardly from a portion of the outer peripheral surface thereof. In addition to the scope 1, the positioning jig 101 shown in FIG. 5 also comprises a probe holder 6 comprising a cylindrical body 6a having a hollow H defined therein of a diameter substantially equal to the outer diameter of the scope 1 and also having distal and proximal ends opposite to each other. The probe holder 6 also comprises an annular flange-like base 6b connected to or formed integrally with the proximal end of the cylindrical body 6a so as to protrude radially outwardly therefrom. The distal end of the cylindrical body 6a is formed with a generally U-shaped alignment recess 6c extending axially inwardly of the cylindrical body 6a such that when the scope 1 having the pattern-bearing disc 2a is inserted into the hollow H, the positioning pin 1a can be received in the alignment recess 6c. The ring-shaped double-sided adhesive sheet 5 is bonded to an annular surface of the flange-like base 6b which is brought into contact with the hand palm.

Figure 6A:
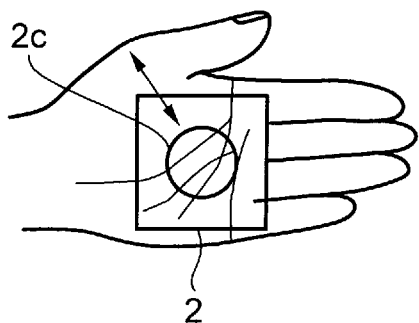
FIGS. 6A to 6F are illustrations showing the sequence of how substantially the same target part of the living body can be aligned with the measurement probe with the use of the positioning jig shown in FIG. 5.

The manner by which the measuring probe 11 is positioned relative to the target area with the use of the positioning jig 101 shown in FIG. 5 will now be described with particular reference to FIGS. 6A to 6F. It is, however, to be noted that FIGS. 6A to 6C are substantially identical with FIGS. 3A to 3C, respectively, and therefore, the scope 1 having the pattern-bearing disc 2a is prepared in a manner similar to that shown in and described with reference to FIGS. 3A to 3C. Accordingly, the description will start from the step shown in FIG. 6D.

Figure 6D:
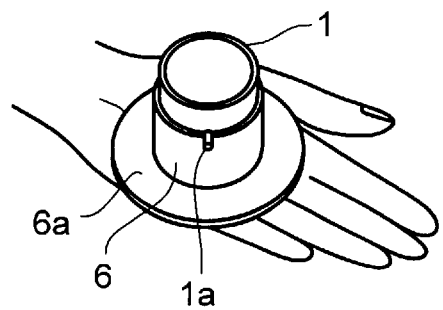
Figure 6B:
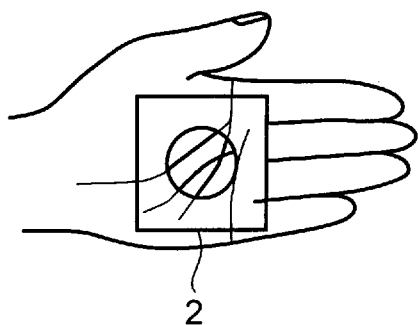

As is the case with the placement of the sheet ring 4 on the hand palm in the foregoing embodiment, the probe holder 6 accommodating the scope 1 inside the hollow H with the positioning pin 1a engaged in the alignment recess 6c is placed on the hand palm as shown in FIG. 6D. At this time, the scope 1 together with the probe holder 6 has to be adjusted in position so that the palm line images on the pattern-bearing disc 2a can exactly align with the respective live palm lines which have been utilized to depict the palm line images on the transparent sheet 2. This can be readily accomplished by looking at the pattern-bearing disc 2a with naked eyes through the hollow of the scope 1.

Figure 6E:
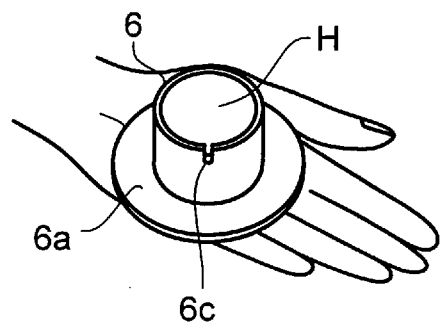
Figure 6C:
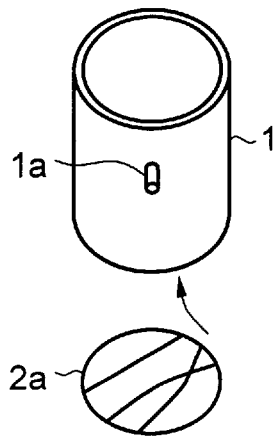

After the positioning of the scope 1 relative to the hand palm, the probe holder 6 having the double-sided adhesive sheet 5 sticking to the flange-like base 6b is placed on and bonded to the hand palm and the scope 1 is subsequently removed out of the probe holder 6 as shown in FIG. 6E. The measurement probe 11 is then inserted into the hollow H of the probe holder 6. In this way, the measurement probe 11 can be reproducibly positioned relative to the target area. However, if the measurement probe 11 is provided with a similar positioning pin 11d as shown in FIG. 6F for engagement in the alignment recess 6c in the probe holder 6, the measurement probe 11 can be exactly positioned in the same orientation not only with respect to the axial direction thereof, but also with respect to the angular direction about the longitudinal axis thereof throughout cycles of biodata measurement.

A first cycle of biodata measurement is performed with the measurement probe 11 received within the probe holder 6 then positioned on the hand palm in the manner described above and shown in FIG. 6F. After this first cycle of measurement, the scope 1 used is labeled and then stored for the time to come to perform a subsequent cycle of biodata measurement. The probe holder 6 may be disposed of if it be made of an inexpensive plastic molding material.

Figure 6F:
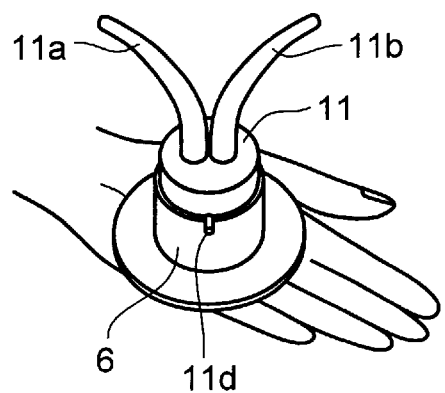

When time comes to perform the subsequent cycle of biodata measurement, the scope 1 once stored should be re-used and the sequence from the step shown in FIG. 6D to the step shown in FIG. 6F is repeated. This is true even when further cycles of biodata measurement are to be individually performed on a chronological basis. Thus, it will readily be seen that each time the target area of the living body is measured, the measurement probe 11 can be positioned reproducibly in an exact location, thereby enabling substantially the same target area to be reexamined.

Figure 7:
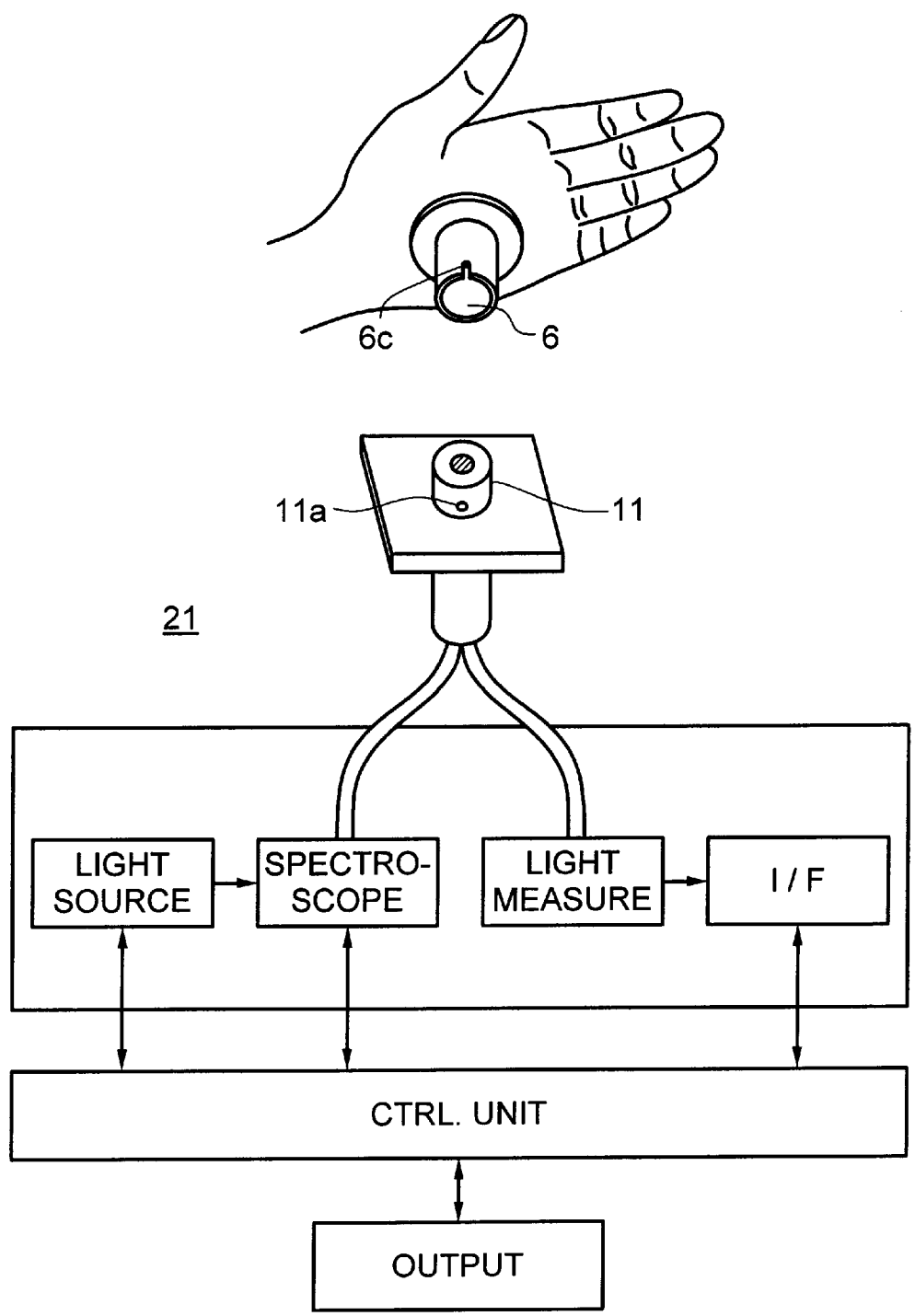
FIG. 7 is a block diagram showing the optical biodata measuring apparatus in which the positioning jig of FIG. 5 is employed.

FIG. 7 illustrates the manner of use of the probe holder 6 in relation to the biodata measuring device 21 and even during this time, the hand to which the probe holder 6 adheres is placed on the support plate while the probe holder 6 is capped onto the proximal end of the measurement probe 11 with the positioning pin 11a engaged in the alignment recess 6c.

Figure 8:
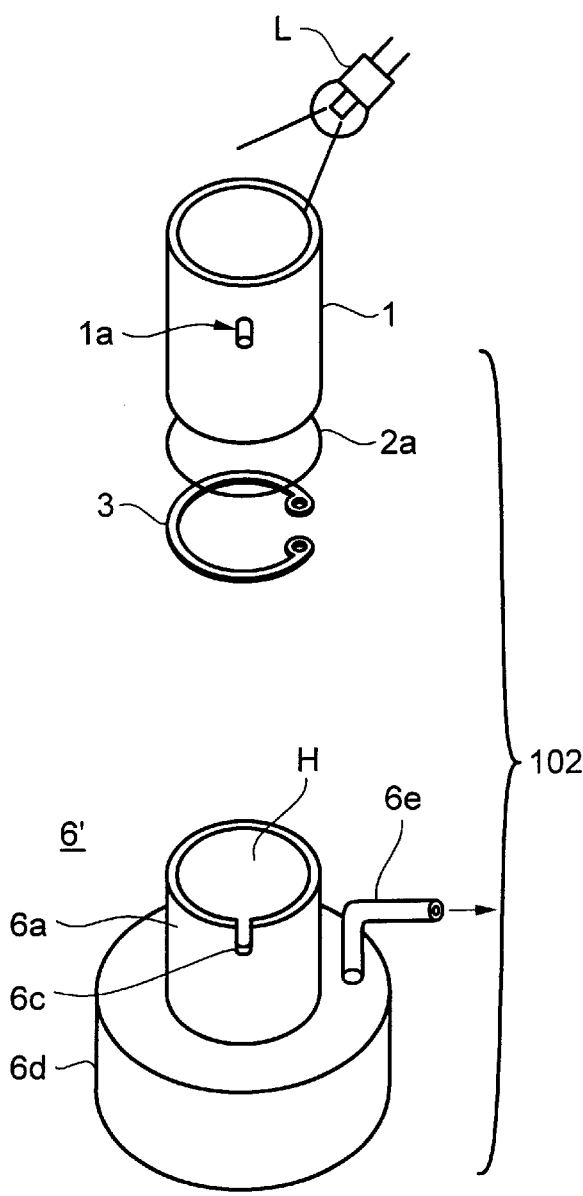
FIG. 8 is an exploded view of the positioning jig according to a third embodiment of the present invention.

FIG. 8 illustrates the positioning jig 102 according to a third embodiment of the present invention. The positioning jig 102 shown in FIG. 8 makes use of a probe holder similar to the probe holder 6 shown in FIG. 5, but differing therefrom in that the probe holder 6' is provided with an annular suction base 6d in place of the annular flange-like base 6b used in the probe holder 6. More specifically, the flange-like base 6d has an annular cavity (not shown) defined therein and communicated with a source of vacuum (not shown) by means of a suction pipe 6e. Accordingly, it will readily be seen that after the probe holder 6' has been placed on the hand palm and the annular cavity in the probe holder 6' is evacuated, the probe holder 6' can be sucked onto and retained in position on the hand palm. The probe holder 6' can be equally utilized in a manner similar to that shown in FIGS. 6D to 6F and FIG. 7. It is to be noted that the source of vacuum may comprise a suction pump that may be powered by a battery and may therefore be compact in structure.

The measurement probe 11 employed in any one of the foregoing embodiments of the present invention would be, or is, of a size about 22 mm in diameter. While although not exclusively, the foregoing embodiments may be applicable where the measurement probe 11 has a relatively large size, the use of a similar measurement probe of a size smaller than that may be contemplated. If the smaller measurement probe is used and the pattern-bearing disc 2a has a correspondingly small diameter to suit to the smaller measurement probe, alignment of the line images on the pattern-bearing disc 2a with the live palm lines would be difficult to accomplish.

Figure 9A:
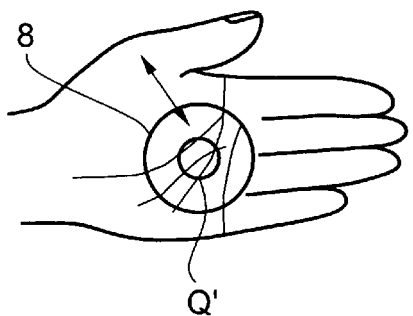
FIGS. 9A to 9C are illustrations showing the sequence of how substantially the same target part of the living body can be aligned with the measurement probe with the use of the positioning jig according to a fourth embodiment of the present invention.
Figure 9B:
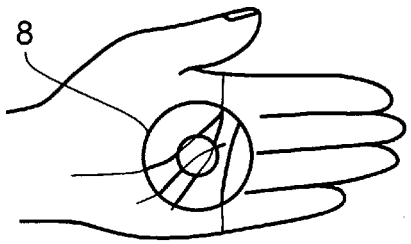
Figure 9C:
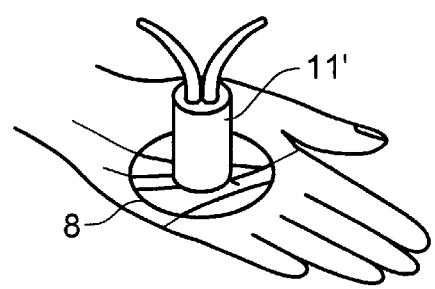

The following embodiment which will be described with particular reference to FIGS. 9A to 9C is intended to provide the positioning jig utilizable in connection with the measurement probe 11 of a relatively small size.

According to this fourth embodiment, as shown in FIG. 9A, reference numeral 8 represents a sheet ring of about 5 cm in outer diameter and having a center hole Q' of about 6.5 mm in diameter defined therein. This sheet ring 8 may be prepared from a transparent sheet in a manner substantially similar to or identical with preparation of the sheet ring 4, that is, by cutting the transparent sheet into a round sheet and then by cutting a center portion from the round sheet, it being, however, to be noted that the center portion removed from the round sheet has no palm print reproduced thereon.

The sheet ring 8 is placed and positioned on the hand palm with the center hole Q' encompassing some of the live palm lines which are distinctive and, at the same time, characteristic of a particular patient. This sheet ring 8 need be stored for subsequent use after a first cycle of biodata measurement and is, therefore, to be fixed to the hand palm by the use of, for example, one or two lengths of a single-sided or double-sided adhesive tape.

After the placement of the sheet ring 8 on the hand palm, and as shown in FIG. 9B, at least the distinctive and characteristic palm lines that extend outwardly from those encompassed within the center hole Q' are reproduced onto the sheet ring 8, in a manner substantially similar to the preparation of the pattern-bearing disc 2a in any one of the foregoing embodiments. Thereafter, as shown in FIG. 9C, the compact measurement probe 11' is mounted on the hand palm with its proximal end snugly received within the center hole Q', followed by start of the first cycle of biodata measurement.

After the first cycle of biodata measurement, the pattern-bearing sheet ring 8 is labeled and stored for subsequent use. When the subsequent cycle or cycles of biodata measurement is or are to be performed, the procedure has to start with the step shown in FIG. 9B, that is, with placement of the pattern-bearing sheet ring 8 on the hand palm of the same patient.

In any one of the foregoing embodiments of the present invention, reference has been made to that portion of the hand palm as the target part of the living body and also to the distinctive and characteristic palm lines as a unique marking that provides a cue to the specific location on the living body. However, the target part may not be always limited to that described and shown and may be any other area of the living body. Similarly, the unique marking that provides the cue to the specific location on the living body may not be limited to that described and shown and may be blood vessels, joints, moles, and/or scars. Also, the biodata measurement in which the method and the device of the present invention can be used may include a glucose concentration measurement, a subcutaneous fat measurement and a blood pressure measurement and, accordingly, the measuring means may not be limited to the measurement probe such as shown and described, but may be any instrument regardless of whether it is used in an invasive measurement or a noninvasive measurement.

Where the target area is a portion of the palm of a patient's hand such as in any one of the foregoing embodiments, application of the measurement probe to the hand palm could be ascertained with naked eyes and, therefore, the biodata measurement has been described as applying the measurement probe to the target area. However, where the target area is a portion of, for example, a patient's foot, difficulty would be encountered with ascertaining the angle at which the measurement probe is disposed relative to the target area and/or accurate measurement would hardly be accomplished if the foot is unconsciously moved. In such case, the use of an auxiliary fixing unit would be necessitated. One example of such auxiliary fixing unit is shown in FIGS. 10 to 13 and will now be described.

Figure 10:
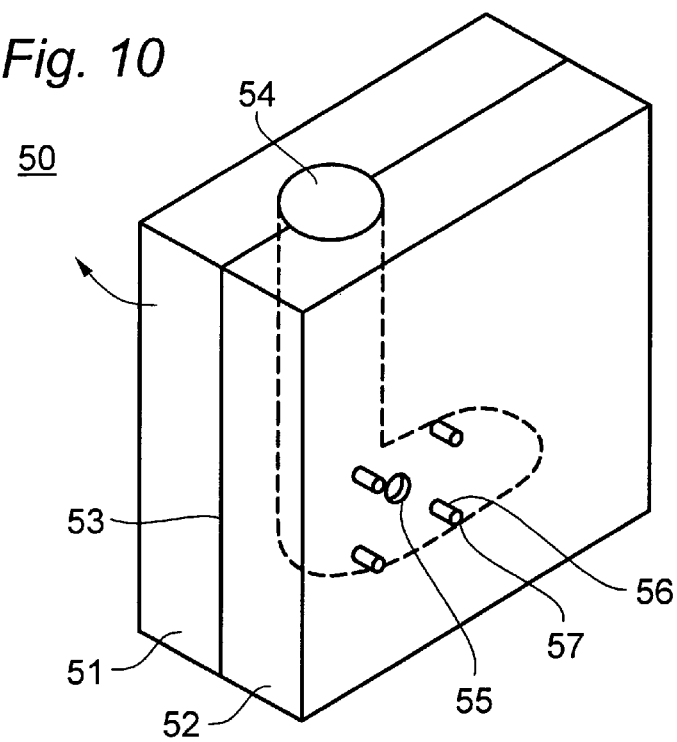
FIG. 10 is a schematic perspective view of a first embodiment of an auxiliary fixing unit.

Referring first to FIG. 10, the auxiliary fixing unit 50 intended to fix the foot comprises first and second molds 51 and 52 made of silicone resin. The first and second molds 51 and 52 are formed respectively with generally L-shaped recesses and have respective mating surfaces 53 which when the first and second molds 51 and 52 are combined together with the mating surfaces 53 closed together as shown, the L-shaped recesses define a foot-shaped mold cavity 54 for generally loosely accommodating therein the foot to be examined.

One of the first and second molds, for example, the second mold 52 is formed with a through-hole 55 extending completely across the thickness thereof with one end opening into the associated L-shaped recess and with the opposite opening at a surface of the second mold 52 opposite to the first mold 51. A plurality of, for example, four support pins 56 each having an axially inwardly extending, internally threaded hole 57 defined in one end thereof are fixedly connected thereto with their opposite ends embedded in the wall of the second mold 52 while extending outwardly from and perpendicular to that surface of the second mold 52.

Figure 11:
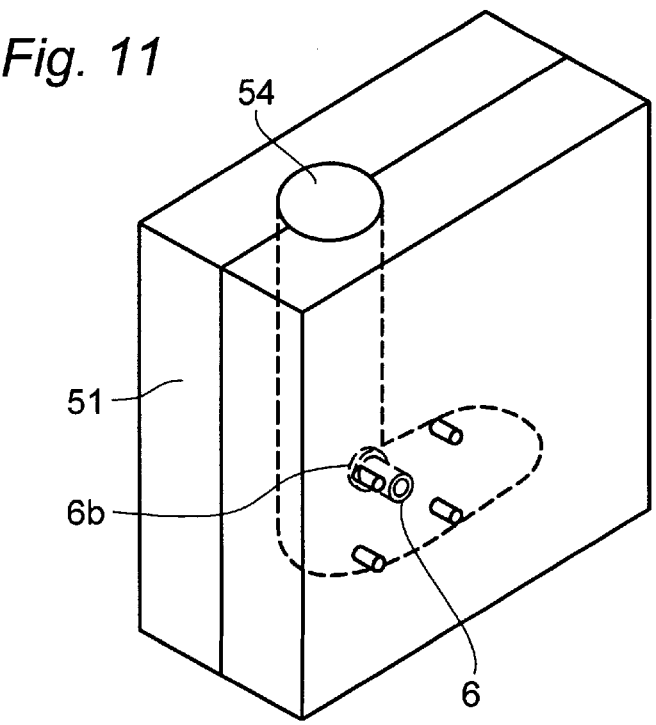
FIG. 11 is a view similar to FIG. 10, in which a probe holder for the measurement probe is mounted in the auxiliary fixing unit of FIG. 10.

The support pins 56 are arranged around the opening of the through-hole 55 on that surface of the second mold 52, preferably spaced an equal distance radially outwardly from and, also, circumferentially about the center of that opening of the through-hole 55. The probe holder 6 of the structure shown in and described with reference to FIG. 5 is mounted in the through-hole 55 with the flange-like base 6b positioned on one side of the wall of the second mold 52 adjacent the foot-shaped mold cavity 54 as shown in FIG. 11. As a matter of course, however, the mounting of the probe holder 6 is carried out while the first and second molds 51 and 52 are separated from each other.

Figure 12:
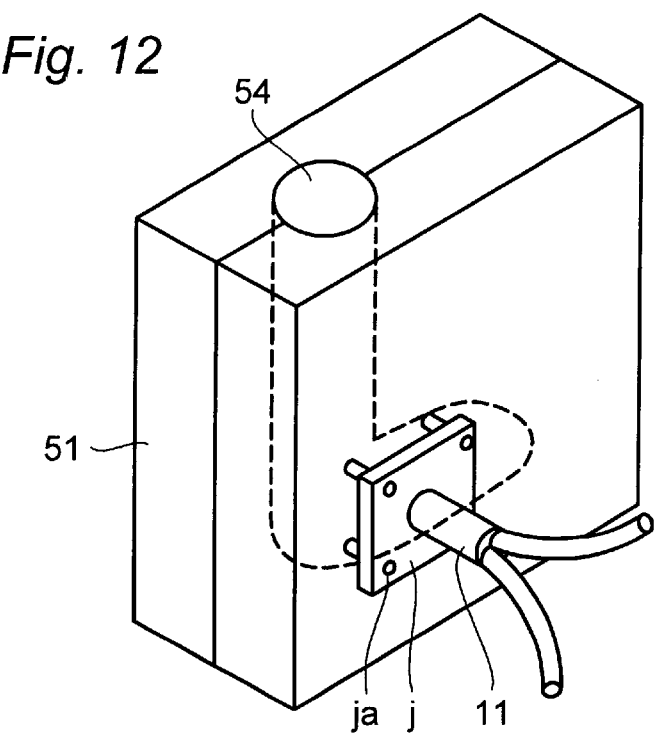
FIG. 12 is a view similar to FIG. 10, showing the measurement probe mounted in the auxiliary fixing unit of FIG. 11.
Figure 13:
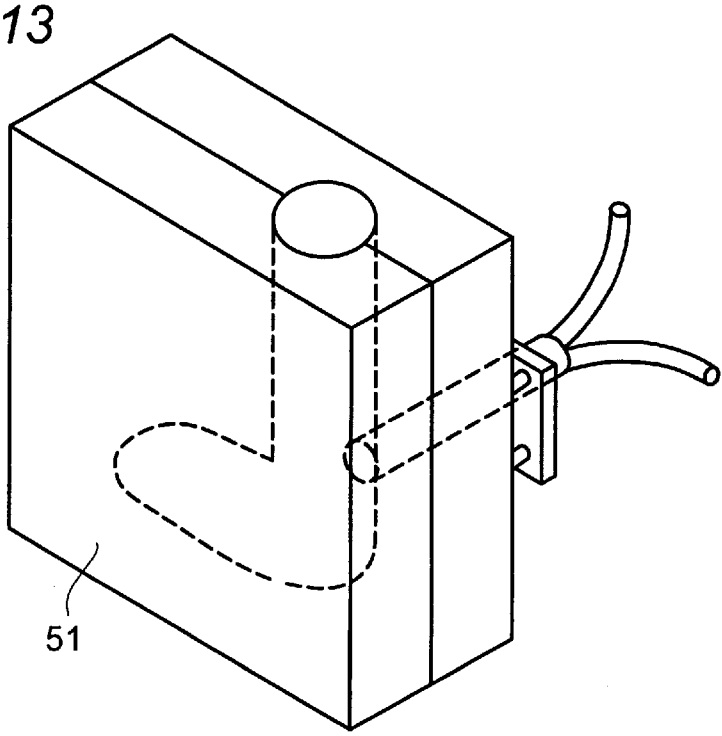
FIG. 13 is a schematic perspective view of the auxiliary fixing unit as viewed from rear, that is, from an angle different from that of FIG. 12.

As shown in FIG. 12, the measurement probe 11 is provided with a generally rectangular support plate J protruding substantially radially outwardly from a portion thereof adjacent the proximal end. This support plate J has holes Ja defined at four corner areas thereof for passage of the corresponding the support pins 56 therethrough. Thus, it will readily be seen that the measurement probe 11 is mounted on the auxiliary fixing unit 50 with the support pins 57 received in the corresponding holes Ja in the support plate J, the proximal end of the measurement probe 11 can pass through the through-hole 55 in the second mold 52 as shown in FIG. 13.

When in use, assuming that the first and second molds 51 and 52 are separated from each other, the rectangular transparent sheet 2 is applied to that surface of the flange-like base 6b which confronts the mold cavity 54, followed by application of the second mold 52 to the patient's foot. Thereafter, the first mold 51 is fitted to the second mold 52 while the patient's foot is half accommodated in the recess in the second mold 52, and the first and second molds 51 and 52 are then closed together. After the closure of the first and second molds 51 and 52 together, the unique marking found in a portion of the foot that is encompassed by the probe holder 6, then received in the through-hole 55 in the second mold 52, is reproduced onto the transparent sheet 2 while such unique marking is viewed with naked eyes through the probe holder 6.

Thereafter, the first and second molds 51 and 52 are separated from each other, followed by removal of the transparent sheet 2 from the flange-like base 6b so that the pattern-bearing disc 2a can be eventually obtained by cutting the transparent sheet 2 in the manner described hereinbefore. The pattern-bearing disc 2a is then fitted to the scope 1 in the manner described hereinbefore by the use of the C-shaped clip ring 3 as shown in FIG. 5.

When a first cycle of biodata measurement is to be performed, and after the first and second molds 51 and 52 are again closed together with the patient's food accommodated within the mold cavity 54, the scope 1 having the pattern-bearing disc 2a fitted thereto is inserted into the probe holder 6. Subsequently, by looking with naked eyes through the scope 1 received in the probe holder 6, the pattern on the pattern-bearing disc 2a has to be aligned with the unique marking on the patient's foot that has been used to form the pattern-bearing disc 2a, while the patient's foot is adjusted in position within the mold cavity 54 or the auxiliary fixing unit 50 is finely moved relative to the patient's food received within the mold cavity 54.

Once the alignment has been successfully done, the scope 1 is removed out of the probe holder 6 and the measurement probe 11 having the support plate J is subsequently mounted in the manner as shown 12, followed by start of the first cycle of biodata measurement in the manner as hereinbefore described.

As hereinbefore fully described, the positioning method and the positioning device of the present invention are such that the biological measurement probe can be positioned reproducibly at the target part of the living body to enable the biological measuring probe to be repeatedly positioned at substantially the same target part, by transferring the unique marking found in the target area of the living body onto the transparent sheet so that the measuring means can be associated with the transparent sheet bearing the unique marking.

Although the present invention has been described in connection with the preferred embodiments thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A method of accurately positioning a measuring means such as a measurement probe relative to a target area of a living body, said target area having a unique marking peculiar to the living body, said method comprising the steps of:

applying a transparent sheet member to the target part;

transferring an image of the unique marking to the transparent sheet member; and associating the measuring means with the transparent sheet member bearing the image of the unique marking so that a subsequent measurement can be performed by the measuring means after the image transferred onto the transparent sheet member has been aligned with the unique marking in the target area.

2. The method according to claim 1 further comprising:

mating a first hollow mold and second hollow mold together with a target area sandwiched in between to render the target area immobile; and providing a through-hole in one of said molds for receiving the positioning member.

3. A device for accurately positioning a measuring means such as a measurement probe relative to a target area of a living body, said target area having a unique marking peculiar to the living body, said device comprising:

a positioning member having a hole defined therein for accommodating the measuring means;

a substantially cylindrical scope having distal and proximal ends opposite to each other and capable of being received in the hole in the positioning member; and a pattern-bearing member bearing an image of the unique marking in the target area of the living body, said pattern-bearing member being adapted to be fitted to the proximal end of the cylindrical scope;

whereby when a measurement is to be performed, the image on the pattern-bearing member is aligned with the unique marking to enable the same target area to be remeasured each time measurement is performed by the measuring means.

4. The device as claimed in claim 3, wherein said positioning member is a transparent sheet ring.

5. The device as claimed in claim 3, wherein said positioning member comprises a tubular member for receiving the measuring means when the latter is inserted in the tubular member, said tubular member having distal and proximal ends opposite to each other, and a flat ring member provided at the proximal end of the tubular member.

6. The device as claimed in claim 4, further comprising a double-sided adhesive member for fixedly attaching the positioning member to the target area.

7. The device as claimed in claim 3, wherein said positioning member comprises a tubular member for receiving the measuring means when the latter is inserted in the tubular member, said tubular member having distal and proximal ends opposite to each other, and an annular suction base provided at the proximal end of the tubular member.

8. The device according to claim 3 further comprising an auxiliary fixing unit including a first and second molds adapted for mating together with the target area sandwiched therebetween to make the target area immovable, said first and second molds having respective recesses which, when the first and second molds are mated together, define a mold cavity generally coextensive with the target area, one of said first and second molds having a through-hole for receiving the positioning member.

9. A device for accurately positioning a measuring means such as a measurement probe relative to a target area of a living body, said target area having a unique marking peculiar to the living body, said device comprising:

a positioning member in the form of an annular transparent sheet having a hole defined therein for accommodating the measuring means, said positioning member having an image of the unique marking transferred thereto, such that during a measurement the image on the positioning member is aligned with the unique marking to enable the same target area to be remeasured each time measurement is performed by the measuring means.

10. A device for positioning a probe relative to a biological body, the device comprising:

a scope having ends and a perimeter;

a pattern-bearing disc attached to or near one of the ends, the pattern-bearing disc having a pattern coinciding with a distinguishing visually apparent feature of a target area of the biological body; and an alignment member having an opening for receiving the perimeter of the scope, the alignment ring associated with an adhesive for adhering the alignment member to the biological body.

11. The device according to claim 10, wherein the scope has a generally tubular perimeter with an exterior diameter, the opening being generally circular with an interior diameter dimensionally corresponding to the exterior diameter for interlocking engagement therewith.

12. The device according to claim 10, wherein the probe includes an optical measuring device with a generally cylindrical housing for engaging the opening of the alignment member.

13. The device according to claim 10, wherein the pattern-bearing disc comprises a transparent film with an adhesive backing for adhering to the target area of the biological body.

14. The device according to claim 10, further comprising a light source for inputting light into an end of the scope opposite an end nearest the pattern-bearing disc.

15. The device according to claim 10, wherein the alignment member comprises a ring having a first layer with a height sufficient to mechanically engage the perimeter of the scope and a second layer coated with adhesive on opposite sides.

16. The device according to claim 10, further comprising a ringlike retainer for attaching the pattern-bearing disc to an end of the scope.

* * * * *